US00PP17048P2

(12) United States Plant Patent
Kordes

(10) Patent No.: US PP17,048 P2
(45) Date of Patent: Aug. 22, 2006

(54) ROSE PLANT NAMED 'KORQUELDA'

(50) Latin Name: *Rosa hybrida*
Varietal Denomination: KORquelda

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/071,757

(22) Filed: Mar. 2, 2005

(51) Int. Cl.
*A01H 5/00* (2006.01)

(52) U.S. Cl. ..... Plt./104

(58) Field of Classification Search ..... Plt./104
See application file for complete search history.

(56) References Cited

PUBLICATIONS

Gemman PBR Application, ROS 2398, Apr. 5, 2004, W. Kordes' Sohne.
QZ (CPVO) Application, 20041558, Aug. 19, 2004, W. Kordes' Sohne.

*Primary Examiner*—Kent Bell
*Assistant Examiner*—June Hwu

(57) ABSTRACT

A new and distinct variety of rose with long lasting, novel yellow flowers, and dark green and attractive foliage. It exhibits upright and uniform growth with abundant flowers. The new variety propagates well using traditional methods. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORquelda'.

BACKGROUND OF THE INVENTION

The new variety of rose plant of the present invention originated from a controlled crossing during the summer of 1995 between an un-named seedling and 'KORruge', a non-patented rose.

The resulting seeds were planted during the following winter and germinated in the spring. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORquelda'.

SUMMARY OF THE INVENTION

The new rose plant may be distinguished from its seed parent, an un-named seedling, by the following combination of characteristics:

1. 'KORquelda' has more vigorous growth, and
2. 'KORquelda' has better disease resistance.

The new rose plant may be distinguished from its pollen parent, KORruge by the following combination of characteristics:

1. 'KORquelda' has more vigorous growth,
2. 'KORquelda' has greater fragrance.

The objective of the hybridization was to create a new and distinct rose plant with unique qualities, such as:

1. Uniform upright growth and abundant flowering;
2. Abundant attractive, recurrent flowers;
3. Semi-glossy to glossy, attractive and abundant foliage, and;
4. Very good resistance to diseases encountered in landscapes and gardens.

This combination of qualities is not present in prior rose cultivars. These objectives have been substantially achieved and in that distinguish 'KORquelda' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORquelda' was selected in May, 1996 from the seedling beds to be asexually propagated for further evaluation. The first asexual propagation of 'KORquelda' was done by budding to seedling understocks in July, 1996 at the W. Kordes Söhne Nursery in Offenseth-Sparrieshoop, Germany.

These initial and subsequent propagations conducted in controlled environments show that the foregoing and all other characteristics of 'KORquelda' come true to form and are transmitted through succeeding generations.

BRIEF DESCRIPTION OF THE DRAWING

The accompanying color illustration shows as true as is reasonably possible to obtain in color photographs of this type, the typical characteristics of the buds and flowers of 'KORquelda'. Specifically illustrated in SHEET ONE is an image of the flowers of 'KORquelda'.

DETAILED BOTANICAL DESCRIPTION

The following is a description of 'KORquelda', as observed in its growth in a nursery in Sparrieshoop, Germany on plants of 2 years age. Color references are made using The Royal Horticultural Society (London, England) Colour Chart, 2001 except where common terms of color are used.

For a comparison, several physical characteristics of the rose variety 'KORpriva', a non-patented rose variety are compared to 'KORquelda' in Chart 1.

CHART 1

| | 'KORquelda' | 'KORpriva' |
|---|---|---|
| Petal count | Very double. | Double. |
| Overall height | 100–125 cm. | 150–190 cm |
| Flowers per stem. | 3–6 blooms/stem. | Generally singly. |

Parents:

*Seed parent.*—Un-named seedling.

*Pollen parent.*—'KORruge'.

Classification:

*Botanical classification.*—*Rose hybrida* 'KORquelda'.

*Commercial classification.*—Shrub rose.

FLOWER AND FLOWER BUD

Blooming habit: Recurrent.

Flower bud:

*Size.*—Upon opening, 25–30 mm in length from base of receptacle to end of bud.

*Bud form.*—Pointed ovoid and long.

*Bud color.*—As sepals first unfold, bud color is Green Yellow Group 1B. When ¼ open, the upper and lower surface of petals is Yellow Group 2C. Guard petals present, color is Green Yellow Group 1C with red intonations on the petal margins Greyed-Green Group 179A.

*Sepals.*—Size: Average 32–40 mm long×8–10 mm wide. Shape: Moderate foliaceous appendages on three of the five sepals. Base is flat at union with receptacle. Quantity: Five. Surface texture: Stipitate glands are present in moderate numbers on margins of sepals with appendages. Margins are nearly smooth, on the sepals with out appendages. Upper surfaces pubescent. Lower surfaces with limited numbers of fine white hairs and a few stipitate glands. Color: Upper surface Yellow Group 144A. Lower surface Green Group 138B.

Receptacle:

*Surface.*—Smooth.

*Color.*—Green Group 138B. Limited intonations of Greyed-Purple Group 183C and Greyed-Purple Group 181A.

*Shape.*—Funnel.

*Size.*—6–10 mm (h)×10–12 mm (w).

Peduncle:

*Surface.*—Smooth. Stipitate glands few to moderate in numbers.

*Length.*—60–90 mm average length.

*Diameter.*—2–3 mm average diameter.

*Color.*—Green Group 138B. Intonations of Greyed-Purple Group 183C and Greyed-Purple Group 181A.

*Strength.*—Moderately strong.

*Borne.*—Multiple flower buds per stem, generally 3 to 6.

Flower bloom:

*Fragrance.*—Little to none.

*Duration.*—3–6 days. As a cut flower, 3 to 5 days.

*Size.*—Medium flowered garden rose. Average flower diameter is 60–70 mm when open.

*Form.*—Shape of flower when viewed from the side: Upon opening, upper part: Convex. Upon opening, lower part: Convex. Open flower, upper part: Flattened convex. Open flower, lower part: Flattened convex.

Color:

*Upon opening, petals.*—Outermost petals: Outer Side: Yellow Group 3B. Inner Side: Lower half of petal is Yellow Group 3B. Upper half of petal is Yellow Group 5A. Innermost petals: Outer Side: Yellow Group 3B. Inner Side: Lower half of petal is Yellow Group 3B. Upper half of petal is Yellow Group 5A.

*Upon opening, basal petal spots.*—Basal petal spot, outermost petals: Outer Side: Yellow Group 12C. Inner Side: Yellow Group 12C. Basal petal spot, innermost petals: Outer Side: Yellow Group 12C. Inner Side: Yellow Group 12C.

*After opening, petals.*—Outermost petals: Outer Side: Yellow Group 3C. Inner Side: Yellow Group 3C. Innermost petals: Outer Side: Yellow Group 3C. Inner Side: Yellow Group 3C.

*After opening, basal petal spots.*—Basal petal spot, outermost petals: Outer Side: Yellow Group 12C. Inner Side: Yellow Group 12C. Basal petal spot, innermost petals: Outer Side: Yellow Group 12C. Inner Side: Yellow Group 12C. Variegations: None.

General tonality: On open flowers Yellow Group 5A. No change in the general tonality at the end of the $5^{th}$ day. Afterwards, general tonality is Yellow Group 5D.

Petals:

*Petal count.*—Approximately 40 petals under normal conditions.

*Petal reflex.*—Petals reflex somewhat.

*Petal edge.*—Entire.

*Petal shape.*—Round. Shape of base is rounded.

*Petal size.*—28–34 mm long; 18–32 mm wide.

*Thickness.*—Average.

*Petal arrangement.*—Generally in a regular pattern with overlapping edges.

*Petaloids.*—Present. Average 6–8 per flower. Petaloids are 16–20 mm long and 10–14 mm wide. Color of inner side is Green Yellow Group 5B. Color of outer side is Yellow Group 5B. Surface texture is wrinkled. Edge is uneven. Shape is linear to elliptic.

Reproductive organs:

*Pistils*—Average. Approximately 80–85 present. Stigmas: Location: At same position as anthers. Color: Green Group 138D. Styles: Length: Average length 12 mm long. Color: Yellow Group 150D.

*Stamens.*—Approximately 100 on average and regularly arranged around the styles. Anthers: Size: 3–3.5 mm long. Color: Yellow Orange Group 17B with intonations of Yellow-Green Group 153D. Pollen: Generally present. Color: Yellow-Orange Group 17B. Filaments: Color: Yellow Group 153D. Length: 8–12 mm. Hips: None observed.

THE PLANT

Plant growth: Vigorous. Upright to bushy habit. When grown as a budded nursery plant the average plant height is 125 cm and the average plant width is 60–70 cm.

Stems:

*Stem color.*—Young wood: Green Group 137A with intonations of Greyed-Purple Group 183C. Older wood: Green Group 137A.

*Stem surface.*—Young wood: Smooth. Older wood: Smooth, with some vertical raised ridges.

Prickles: Present.

*Incidence.*—Approximately 8 per 10 cm of stem.

*Size.*—Average length: 6–7 mm, with some to 9 mm. Occasionally numerous smaller prickles, 1–3 mm in length.

*Color.*—Immature and mature prickles Greyed-Red Group 178A. Anthocyanin present on most thorns, Greyed-Green Group 178A to Greyed-Purple Group 183C.

*Shape.*—Larger prickles deeply concave, while smaller prickles tend to be linear.

Leaves and leaflets: Normally 5 leaflets on normal leaves in middle of the stem.

*Leaf size.*—140 mm (l)×110 mm (w).

*Quantity.*—Above average abundance.

*Texture.*—Upper side glossy. Thick. Leathery.

*Color, mature foliage.*—Upper Leaf Surface: Green Group 137A. Lower Leaf Surface: Green Group 138A.

*Color, juvenile foliage.*—Upper Leaf Surface: Green Group 138A. Lower Leaf Surface: Green Group 138B.

*Anthocyanin intonation.*—Generally present. Greyed-Green Group 178A to Greyed-Purple Group 183C. Location: Leaf margins, edges, and underside.

Stipules:

*Size.*—25 mm (l)×6 mm (w).

*Stipule color.*—Green Group 138A with some intonations of Greyed-Purple Group 183C.

*Presence of stipitate glands.*—Abundant on margins.

*Margins.*—Bearded.

Petiole:

*Length.*—8 mm–20 mm.

*Diameter.*—1.5–2.0 mm average diameter.

*Petiole color.*—Green Group 138A. Underneath: Green Group 138A. Anthocyanin: Abundant. Greyed-Purple Group 183A.

*Prickles.*—A few small prickles.

*Stipitate glands.*—Present on margins.

Petiole rachis:

*Color.*—Green Group 138A.

*Prickles.*—A few prickles present.

*Stipitate glands.*—Generally along margins.

Leaflets:

*Size.*—Average terminal leaf size 65 mm (l)×45 mm (w).

*Shape.*—Pointed oval. Leaflet base: Rounded. Leaflet apex: Acute.

*Margins.*—Serrated.

*Texture.*—Thick to leathery.

Hips/seed formation: None observed.

Winter hardiness observation: To date, the new variety has been grown successfully in Zone 5.

Disease resistance: Very good resistance to black spot, powdery mildew, and rust diseases under normal growing conditions.

I claim:

1. A new and distinct variety of rose plant characterized by the following combination of characteristics:

(a) abundant, attractive long lasting yellow flowers;

(b) an upright to bushy growth habit, and;

(c) very good disease resistance;

substantially as herein illustrated and described.

* * * * *

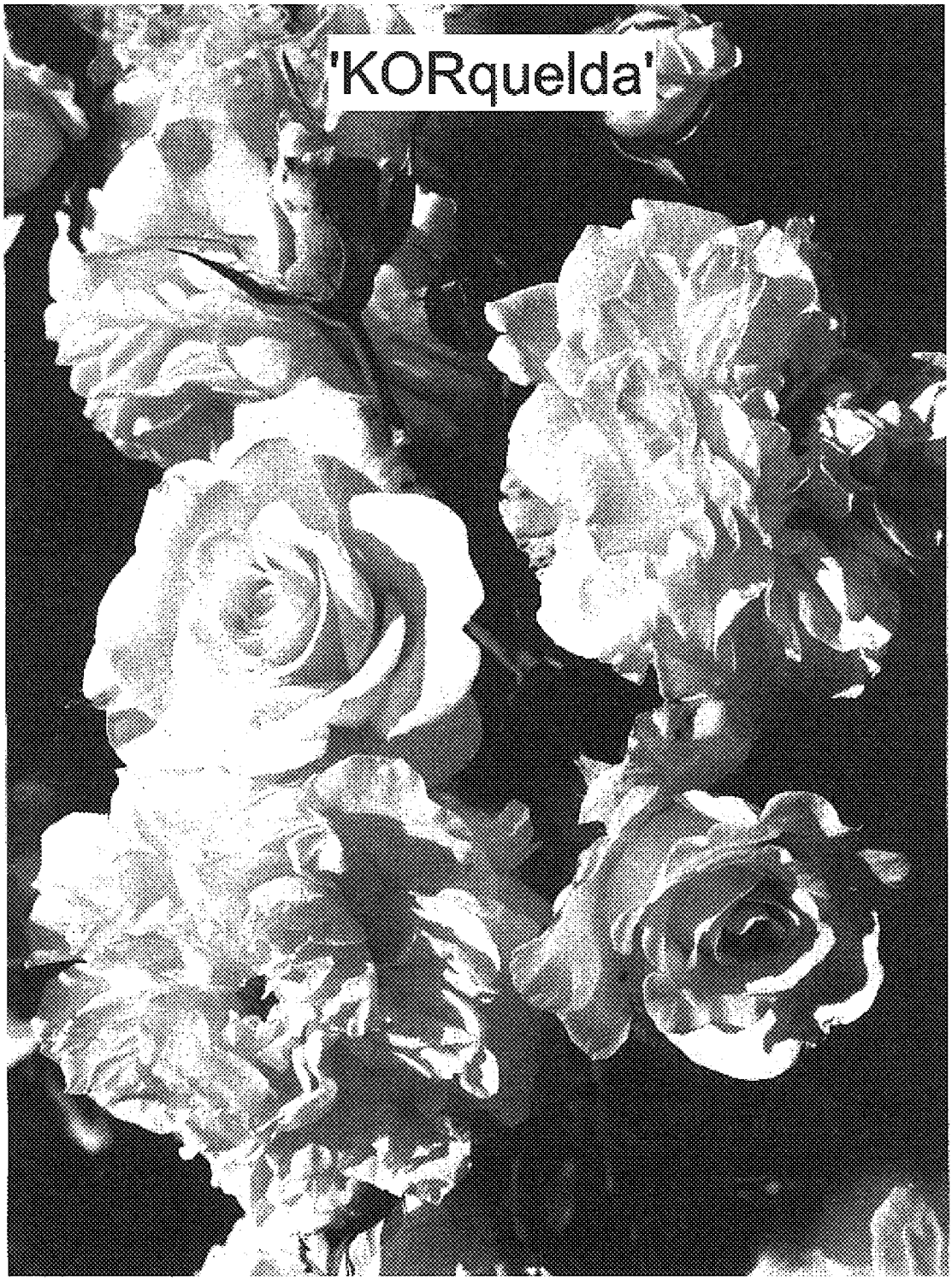
'KORquelda'